United States Patent [19]

Kuriyama et al.

[11] Patent Number: 4,473,708

[45] Date of Patent: Sep. 25, 1984

[54] PREPARATION OF KETOZINES USING ORGANOARSENIC COMPOUNDS

[75] Inventors: Yasuhisa Kuriyama, Tokyo; Minoru Kakuda, Chiba; Shoichi Nitoh, Tokyo, all of Japan

[73] Assignee: Mitsubishi Gas Chemical Company Inc., Tokyo, Japan

[21] Appl. No.: 396,572

[22] Filed: Jul. 9, 1982

[30] Foreign Application Priority Data

Jul. 9, 1981 [JP] Japan .............................. 56-107384

[51] Int. Cl.³ .................. C07C 109/12; C07C 109/14; C07C 109/16; C07C 119/00
[52] U.S. Cl. ..................................... 564/249; 502/152
[58] Field of Search ......................... 564/249; 502/152

[56] References Cited

U.S. PATENT DOCUMENTS 3,972,878  8/1976  Schirmann et al. ................. 564/249
4,093,656  6/1978  Schirmann et al. ................. 564/249

Primary Examiner—Natalie Trousof
Assistant Examiner—L. Hendriksen
Attorney, Agent, or Firm—Sughrue, Mion, Zinn, Macpeak & Seas

[57] ABSTRACT

A process for preparing a ketazine useful as an intermediate for the synthesis of hydrazine is disclosed. The process comprises reacting an aliphatic or aromatic ketone with ammonia and hydrogen peroxide in the presence of a catalyst of an arsenic compound to produce a corresponding ketazine.

18 Claims, No Drawings

PREPARATION OF KETOZINES USING ORGANOARSENIC COMPOUNDS

FIELD OF THE INVENTION

This invention relates to a process for preparing a ketazine and, more particularly, to a process for preparing a ketazine which comprises reacting an aliphatic or aromatic ketone with ammonia and hydrogen peroxide in the presence of a catalyst of an arsenic compound.

BACKGROUND OF THE INVENTION

Ketazines are useful as intermediates for the synthesis of hydrazine and various methods for preparing ketazines have been developed and proposed. Recently, studies have been made extensively on the process for preparing ketazines using a ketone, ammonia and hydrogen peroxide as starting materials, and such processes are disclosed, for example, in Japanese patent publication Nos. 33083/76, 36247/76, 37638/76 and 43922/78, and Japanese patent application (OPI) No. 36615/77 (the term "OPI" as used herein refers to a "published unexamined patent application"). The processes proposed in these prior art references comprise reacting the above starting materials in the presence of a nitrile or an amide as a co-reactant as an essential component of the reaction system. However, in these conventional processes, the nitrile or the amide is converted into an amide or an ammonium salt of a carboxylic acid, respectively, as the reaction proceeds, and complicated procedures are required for separation and recovery of the amide or the ammonium salt from the reaction mixture, and also for the reproduction of the nitrile and the amide from these by-products.

Also, processes for preparing ketazines using various catalysts without nitrile or amide have been proposed. For example, Japanese patent publication No. 27642/76 proposes a process using a selenium catalyst, Japanese patent application (OPI) No. 125629/79 proposes a process using a cobalt salt catalyst, Japanese patent application (OPI) No. 135719/79 proposes a process using a palladium catalyst, and Japanese patent application (OPI) No. 135718/79 proposes a process using silica gel catalyst. However, none of these conventional processes using a catalyst has sufficient reaction rate and the selectivity to the desired ketazine and, therefore, these processes are still unsatisfactory in practicing on an industrial scale.

As a result of extensive studies on a process for preparing ketazines efficiently and in high yield, the present inventors found that such objects can be achieved by using a specific arsenic compound as a catalyst.

SUMMARY OF THE INVENTION

An object of the present invention is therefore to provide a process for preparing a ketazine which comprises reacting an aliphatic or aromatic ketone with ammonia and hydrogen peroxide in the presence of an aresenic compound catalyst to provide a corresponding ketazine.

DETAILED DESCRIPTION OF THE INVENTION

The ketone used in the process of this invention can be any ketone compound which is known to form a corresponding ketazine. Examples of ketone compounds are represented by the formula

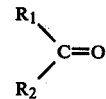

wherein $R_1$ and $R_2$, which may be the same or different, each represents a straight or branched chain alkyl group having not more than 12 carbon atoms, a cycloalkyl group having 3 to 12 carbon atoms or an aryl group having 6 to 12 carbon atoms, or $R_1$ and $R_2$ may form a ring having 4 to 11 carbon atoms when taken together with the carbon atom of the carbonyl group to which they are attached. Such ketone compound can form, upon reaction, a ketazine represented by the formula

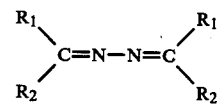

wherein $R_1$ and $R_2$ are as defined above.

Examples of ketones which can be used include acetone, methyl ethyl ketone, 2-pentanone, 3-methyl-2-butanone, 3-methyl-2-pentanone, 4-methyl-2-pentanone, methyl cyclohexyl ketone, benzophenone, cyclopentanone, cyclohexanone, cycloheptanone, cyclooctanone, cyclodecanone, cyclododecanone and the like, but the present invention is not limited to these specific ketone compounds. When the ketazine is prepared for the purpose of producing hydrazine by hydrolyzing the resulting ketazine with water, an alkyl ketone, particularly acetone or methyl ethyl ketone, is preferred as a ketone compound from the economical standpoint since they are easily handled and easily available.

In the process of this invention, the reaction tends to proceed rapidly and the selectivity tends to increase as the water content in the reaction system decreases. Thus, the concentration of hydrogen peroxide used in the form of its aqueous solution for the reaction is preferably as high as possible. Generally, it is advantageous to use an aqueous solution of hydrogen peroxide having a hydrogen peroxide concentration of 30 to 90% by weight, preferably more than 60% by weight. Of course, an aqueous solution having a lower concentration of hydrogen peroxide may be used so long as the water content in the reaction system is maintained at a low level during the reaction while removing water from the reaction system by azeotropic distillation with a solvent which forms an azeotropic mixture with water or while removing water with an entraining gas such as ammonia gas. Alternatively, the water content can be reduced, for example, by adding a dehydrating agent to the reaction system. In another embodiment, a ketone can be previously combined with hydrogen peroxide by the procedure well known in the art to form a peroxide and the resulting peroxide can be used in the reaction in place of ketone and hydrogen peroxide reactants.

The catalyst used in the process of this invention comprises an inorganic arsenic compound, an organoarsenic compound or a mixture thereof, preferably an organoarsenic compound.

Examples of inorganic arsenic compounds are arsenic oxides, arsenic oxyacids, salts or esters of arsenic oxyacids, arsenic halides, arsenic oxyhalides and arsenic sulfides.

Examples of organoarsenic compounds wherein the valency of arsenic is trivalent (+3) include compounds represented by the formula RAsXY, arsenoso compounds [(RAsO)n], primary arsenic oxides [RAsO], heterocyclic derivatives of arsenic such as arsorane

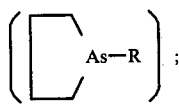

arseno derivatives [(RAs=)₂] and the like, wherein R represents an alkyl group having 1 to 12 carbon atoms, an aralkyl group having 7 to 12 carbon atoms, an aryl group having 6 to 12 carbon atoms, a halogen atom, a hydroxyl group, an alkoxy group having 1 to 12 carbon atoms, an acyloxy group having 1 to 12 carbon atoms, —AsR'R", —OAsR'R", a nitrogen-containing group, for example, —NR'R", a phosphorus-containing group, for example, —PO(OR')₂, a silicon-containing group, for example, —OSiR'₃ or a sulfur-containing group (wherein R' and R", which may be the same or different, each represents an alkyl group having 1 to 12 carbon atoms, an aralkyl group having 7 to 12 carbon atoms or an aryl group having 6 to 12 carbon atoms), n is an integer representing the number of recurring unit in the polymeric structure, and X and Y, which may be the same or different, each represents an alkyl group having 1 to 12 carbon atoms, an aralkyl group having 7 to 12 carbon atoms, an aryl group having 6 to 12 carbon atoms, a halogen atom, a hydroxyl group or an alkoxy group having 1 to 12 carbon atoms.

Examples of organoarsenic compounds wherein the valency of arsenic is pentavalent (+5) includes compounds represented by the formulae R'R"R'"AsXY, R'R"Ar(=O)X and R'"As(=O)XY wherein R', R", X and Y are as defined above, and R'" represents an alkyl group having 1 to 12 carbon atoms, an aralkyl group having 7 to 12 carbon atoms or an aryl group having 6 to 12 carbon atoms which may be the same as or different from R' and R".

Referred organoarsenic compounds are those represented by the formulae R'R"As(=O)X and R'"As(=O)XY, and particularly preferred compounds are organoarsenic acids of the formula R'R"As(=O)OH, and organoarsonic acids of the formula R'"As(=O)(OH)₂ wherein R', R" and R'" are as defined above. Examples of such acids are methylarsonic acid, ethylarsonic acid, phenylarsonic acid, o-, m- and p-methylphenylarsonic acids, o-, m- and p-methoxyphenylarsonic acids, o-, m- and p-carboxyphenylarsonic acids, o-, m- and p-nitrophenylarsonic acids, o-, m- and p-chlorophenylarsonic acids, o-, m- and p-nitrophenylarsonic acids, cacodylic acid (dimethylarsenic acid), diethylarsenic acid, diphenylarsenic acid and the like.

Generally, the higher the catalyst concentration in the reaction system, the higher the reaction rate, but the optimum concentration of the catalyst can be determined depending upon the reaction conditions used and from the economical standpoint. The catalyst is usually used in an amount of about 0.01 to about 5 moles, preferably 0.1 to 1 mole, per mole of hydrogen peroxide.

In the process of this invention, the reaction between ketone, ammonium and hydrogen peroxide proceeds in the presence of a catalyst without using a solvent, but the reaction may be conducted in the presence of an inert organic solvent in order to ensure a uniform reaction system and to reduce a water concentration in the reaction system. Any inert organic solvents can be used in the reaction unless they are not decomposed under the reaction conditions used and they do not take part in the reaction with the reactants and reaction products or do not decompose or otherwise adversely affect the reactants and reaction products. Preferred examples of such solvents are alcohols, esters, ethers, hydrocarbons, halogenated hydrocarbons, sulfonic acids and the like, and the said solvent is used in an amount of about 4 to 40 mols per mole of hydrogen peroxide. Practically, the solvent is selected by taking consideration of such factor as high solubility of reactants, easy separation from the reaction product and low cost, and in general preferred solvents include aliphatic lower alcohols and diols or mixtures of diols and aliphatic lower alcohols. Particularly preferred solvents are diols having 3 to 5 carbon atoms, for example, propylene glycol, 1,3-propanediol, 1,3-butanediol, 1,4-butanediol and 1,5-pentanediol.

Ammonia used in the process of this invention can be introduced in the reaction system in the form of aqueous ammonia or ammonia gas. However, in order to reduce the water content in the reaction system, ammonia is preferably introduced in the form of ammonia gas.

The starting materials, a ketone, ammonia and hydrogen peroxide, can be used in any proportions, but from the standpoints of yield of the desired ketazine and economy, the ketone is preferably used in an amount ranging from about 0.5 to 10 moles, most preferably 1.5 to 5 moles, and ammonia is preferably used in an amount ranging from about 0.5 to about 20 moles, most preferably 2 to 10 moles, per mole of hydrogen peroxide.

However, the maximum amount of ammonia which can be used is spontaneously limited due to its saturation in the reaction system. Therefore, an increased concentration of ammonia in the reaction system by using pressurized reaction conditions or by adding ammonium acetate, etc. to the reaction system is generally very effective for increasing the reaction rate.

The reaction can be conducted in a liquid phase at a temperature of about 0° to about 120° C., preferably 30° to 100° C. under atmospheric pressure or pressurized conditions.

The hydrogen peroxide reactant is relatively unstable and is liable to be decomposed during the reaction by contamination with a foreign material such as a heavy metal, etc. thereby decreasing the yield of the desired ketazine. It is therefore highly desirable to add a stabilizer such as a chelating agent such as ethylenediaminetetraacetic acid, diethylenetriaminepentaacetic acid, cyclohexanediaminetetraacetic acid, aminotrimethylenephosphonic acid, 1-hydroxyethylidene-1,1-diphosphonic acid, ethylenediaminetetramethylenephosphonic acid and the like, to the reaction system to stabilize the hydrogen peroxide reactant.

According to the process of this invention, the desired ketazine can be produced in high selectivity and in high yield and thus the process is very useful for practicing on an industrial scale.

The present invention is further illustrated in greater detail by the following Examples, but they are not to be construed as limiting the present invention. Unless otherwise indicated, all percents are by weight.

EXAMPLE 1

2 g of cacodylic acid was placed in a 100 cc capacity four-necked flask equipped with a refluxing condenser and then 5 ml of propylene glycol, 20 ml of t-butanol and 20 ml of methyl ethyl ketone were charged into the flask. Ammonia gas was then blown into the resulting mixture to a saturation while warming the mixture at 60° C. and stirring. Thereafter, the blowing rate of ammonia gas was adjusted to about 40 cc/minute (S.T.P.) and 20 ml of a t-butanol solution containing 0.056 mole of 60% hydrogen peroxide was added dropwise to the mixture over a period of about 5 minutes. After allowing the mixture to react for 1 hour at 60° C., methyl ethyl ketone azine formed in the reaction mixture was quantitatively determined by gas chromatography and the yield of the product was found to be 6.7 g (0.048 mole) which corresponded to 86% yield based on the hydrogen peroxide used. The reaction mixture was then distilled under reduced pressure so as to leave unreacted cacodylic acid and propylene glycol as a residue in a distillator whereby about 95% of the ketazine contained in the reaction mixture was obtained as a distillate.

The above reaction was repeated using the residue in the distillator to obtain methyl ethyl ketone azine in a yield of 85%.

EXAMPLE 2

2 g of phenylarsonic acid was placed in a 100 cc capacity flask equipped with a refluxing condenser and then 10 ml of ethylene glycol, 20 ml of t-butanol and 20 ml of methyl ethyl ketone were charged into the flask. Ammonia gas was then blown into the resulting mixture to a saturation while warming the mixture at 60° C. and stirring. Thereafter, the blowing rate of ammonia gas was adjusted to about 40 cc/minute (S.T.P.) and 20 ml of a t-butanol solution containing 0.056 mole of 90% hydrogen peroxide was added dropwise to the mixture over a period of about 5 minutes. After allowing the mixture to react for 2 hours at 50° C., methyl ethyl ketone azine formed in the reaction mixture was quantitatively determined by gas chromatography and yield of the product was found to be 6.8 g (0.049 mole) which corresponded to 88% yield based on the hydrogen peroxide used.

EXAMPLES 3 TO 10

These examples were conducted using different solvent systems. The reaction was repeated using the same reaction conditions and procedures as described in Example 2 but using the solvent system shown in Table 1 below in place of the solvent system of ethylene glycol and t-butanol. The results obtained are shown in Table 1 below.

TABLE 1

| Example No. | Solvent System | | Yield of Ketazine (%) |
| --- | --- | --- | --- |
| 3 | Ethylene Glycol | 10 ml | 36 |
|   | Methanol | 40 ml | |
| 4 | Ethylene Glycol | 10 ml | 67 |
|   | Ethanol | 40 ml | |
| 5 | Ethylene Glycol | 10 ml | 86 |
|   | Isopropanol | 40 ml | |
| 6 | Ethylene Glycol | 10 ml | 88 |
|   | Tetrahydrofuran | 40 ml | |
| 7 | Ethylene Glycol | 10 ml | 33 |
|   | Sulforane | 40 ml | |
| 8 | Ethylene Glycol | 10 ml | 71 |
|   | t-Butanol | 20 ml | |
|   | Dichloromethane | 20 ml | |
| 9 | Propylene Glycol | 40 ml | 22 |
| 10 | Isopropanol | 40 ml | 51 |

EXAMPLES 11 TO 13

These examples were conducted using different ketone reactants. The reaction was repeated using the same reaction conditions and procedures as described in Example 2 but using the ketone reactant shown in Table 2 below in place of the methyl ethyl ketone. The results obtained are shown in Table 2 below.

TABLE 2

| Example No. | Ketone Reactant | Yield of Ketazine (%) |
| --- | --- | --- |
| 11 | Acetone | 73 |
| 12 | Cyclohexanone | 89 |
| 13 | Acetophenone | 16 |

EXAMPLES 14 TO 15

These examples were conducted using different reaction temperatures. The reaction was repeated using the same reaction conditions and procedures as described in Example 2 but using the reaction temperatures shown in Table 3 below. The results obtained are shown in Table 3 below.

TABLE 3

| Example No. | Reaction Temperature | Yield of Ketazine (%) |
| --- | --- | --- |
| 14 | 30° C. | 26 |
| 15 | 68° C. | 73 |

EXAMPLES 16 TO 19

These examples were conducted using different catalysts. The reaction was repeated using the same reaction conditions and procedures as described in Example 2 but using the catalyst shown in Table 4 in place of phenylarsonic acid. The results obtained are shown in Table 4 below.

TABLE 4

| Example No. | Catalyst and Amount (g) | | Yield of Ketazine (%) |
| --- | --- | --- | --- |
| 16 | Methylarsonic acid | 0.5 | 74 |
| 17 | p-Nitrophenylarsonic Acid | 0.5 | 58 |
| 18 | Diphenylarsenic Acid | 0.5 | 27 |
| 19 | $As_2O_3$ | 0.5 | 8 |

EXAMPLE 20

The reaction was repeated using the same reaction conditions and procedures as described in Example 2 but using 0.5 g of phenylarsonic acid and additionally 5 g of ammonium acetate. The yield of ketazine was found to be 68%.

EXAMPLE 21

4 g of cacodylic acid and 0.1 g of cyclohexanediamine tetraacetic acid as a stabilizer were placed in a 100 cc capacity four-necked flask equipped with a refluxing condenser and then 4 g of 1,3-butanediol was charged into the flask. Ammonia gas was then blown into the resulting mixture to a saturation while warming the mixture at 60° C. and stirring. Thereafter, 0.24 mole of methyl ethyl ketone and 0.10 mole of hydrogen peroxide were added over a period of 20 minutes with vigorous stirring. During the addition, ammonia gas was absorbed vigorously and additional ammonia gas was supplied to the reaction system continuously to compensate for the consumption during the reaction. After completion of the addition of methyl ethyl ketone and hydrogen peroxide, the reaction mixture was stirred at 60° C. for 3 hours in an ammonia gas stream. After completion of the reaction, methyl ethyl ketone azine was quantitatively determined by gas chromatography and the yield of the product was found to be 12.2 g (0.087 mole) which corresponded to 87% yield based on the hydrogen peroxide used.

While the invention has been described in detail and with reference to specific embodiment thereof, it will be apparent to one skilled in the art that various changes and modifications can be made therein without departing from the spirit and scope thereof.

What is claimed is:

1. A process for preparing a ketazine which comprises reacting a ketone with ammonia and hydrogen peroxide in the presence of an organoarsenic compound as a catalyst, wherein said organoarsenic compound is represented by the formula R'R"As(=O)X or R'"As(=O)XY wherein R', R" and R'", which may be the same or different, each represents an alkyl group having 1 to 12 carbon atoms, an aralkyl group having 7 to 12 carbon atoms or an aryl group having 6 to 12 carbon atoms, and X and Y, which may be the same or different, each represents an alkyl group having 1 to 12 carbon atoms, an aralkyl group having 7 to 12 carbon atoms, an aryl group having 6 to 12 carbon atoms, a halogen atom, a hydroxyl group or an alkoxy group having 1 to 12 carbon atoms.

2. A process according to claim 1, wherein said ketone is represented by the formula

wherein $R_1$ and $R_2$ which may be the same or different, each represents a straight or branched chain alkyl group having 1 to 12 carbon atoms, a cycloalkyl group having 3 to 12 carbon atoms or an aryl group having 6 to 12 carbon atoms, or $R_1$ and $R_2$ may form a ring having 4 to 11 carbon atoms when taken together with the carbon atom of the carbonyl group to which they are attached.

3. A process according to claim 2, wherein said ketone is an alkyl ketone.

4. A process according to claim 2, wherein said ketone is acetone or methyl ethyl ketone.

5. A process according to claim 1, wherein said organoarsenic compound is used in an amount of about 0.01 to about 5 moles per mole of said hydrogen peroxide.

6. A process according to claim 1, wherein said reaction is conducted at a temperature of about 0° to about 120° C. under atmospheric pressure or pressurized conditions.

7. A process according to claim 1, wherein said hydrogen peroxide is used as an aqueous solution of hydrogen peroxide having a hydrogen peroxide concentration of about 30 to about 90% bt weight.

8. A process according to claim 1, wherein said organoarsenic compound is represented by the formula R'R"As(=O)OH or R'"As(=O)(OH)$_2$ wherein R', R" and R'", which may be the same or different, each represents an alkyl group having 1 to 12 carbon atoms, an aralkyl group having 7 to 12 carbon atoms or an aryl group having 6 to 12 carbon atoms.

9. A process according to claim 1, wherein said organoarsenic compound is methylarsonic acid, ethylarsonic acid, phenylarsonic acid, o-, m- or p-methylphenylarsonic acid, o-, m- or p-methoxyphenylarsonic acid, o-, m- or p-nitrophenylarsonic acid, cacodylic acid (dimethylarsenic acid), diethylarsenic acid, or diphenylarsenic acid.

10. A process according to claim 1, wherein said organoarsenic compound is cacodylic acid or phenylarsonic acid.

11. A process according to claim 1, wherein said ketone is used in an amount of about 0.5 to about 10 moles per mole of said hydrogen peroxide.

12. A process according to claim 1, wherein said ammonia is used in an amount of about 0.5 to about 20 moles per mole of said hydrogen peroxide.

13. A process according to claim 1, wherein said reaction is conducted in a solvent selected from the group consisting of alcohols, esters, ethers, hydrocarbons, halogenated hydrocarbons and sulfonic acids.

14. A process according to claim 13, wherein said solvent is an alcohol.

15. A process according to claim 14, wherein said alcohol is a diol.

16. A process according to claim 15, wherein said diol has 3 to 5 carbon atoms.

17. A process according to claim 14, wherein said alcohol is a mixture of at least one aliphatic alcohol having 1 to 4 carbon atoms and at least one diol having 2 to 5 carbon atoms.

18. A process according to claim 13, wherein said solvent is used in an amount of about 4 to about 40 mols per mole of hydrogen peroxide.

* * * * *